US011020004B2

(12) United States Patent
Varkuti

(10) Patent No.: US 11,020,004 B2
(45) Date of Patent: Jun. 1, 2021

(54) OPTIMAL DEEP BRAIN STIMULATION ELECTRODE SELECTION AND PLACEMENT ON THE BASIS OF STIMULATION FIELD MODELLING

(71) Applicant: Brainlab AG, Munich (DE)

(72) Inventor: Bálint Varkuti, Munich (DE)

(73) Assignee: BRAINLAB AG, Munich (DE)

(*) Notice: Subject to any disclaimer, the term of this patent is extended or adjusted under 35 U.S.C. 154(b) by 4 days.

(21) Appl. No.: 16/478,081

(22) PCT Filed: Feb. 28, 2017

(86) PCT No.: PCT/EP2017/054547
§ 371 (c)(1),
(2) Date: Jul. 15, 2019

(87) PCT Pub. No.: WO2018/157909
PCT Pub. Date: Sep. 7, 2018

(65) Prior Publication Data
US 2019/0343389 A1   Nov. 14, 2019

(51) Int. Cl.
*A61B 5/00* (2006.01)
*A61N 1/05* (2006.01)

(52) U.S. Cl.
CPC .......... *A61B 5/0036* (2018.08); *A61N 1/0534* (2013.01)

(58) Field of Classification Search
CPC .................................................. A61N 1/0534
See application file for complete search history.

(56) References Cited

U.S. PATENT DOCUMENTS 7,167,760 B2   1/2007   Dawant et al.
8,160,676 B2   4/2012   Gielen et al.
(Continued)

FOREIGN PATENT DOCUMENTS

WO   2012092511 A2   7/2012
WO   2015149170 A1   10/2015
(Continued)

OTHER PUBLICATIONS

International Search Report and Written Opinion for PCT Application No. PCT/EP2017/054547 dated Nov. 8, 2017.
(Continued)

*Primary Examiner* — Edward Park
(74) *Attorney, Agent, or Firm* — Middleton Reutlinger

(57) ABSTRACT

Disclosed is a computer-implemented medical data processing method for planning a position of an electric stimulation device for neurostimulation of at least two target regions (TV1, . . . , TVN) disposed in an anatomical body part of a patient's body, the electric stimulation device (7) comprising at least two electric contacts, the method comprising executing, on at least one processor of at least one computer (3), steps of: a) acquiring (S1.1), at the at least one processor, medical image data describing a digital image of the anatomical body part, wherein the anatomical body part contains at least two target regions (TV1, . . . , TVN); b) determining (S1.2), by the at least one processor and based on the medical image data, target position data describing a position of each target region (TV1, . . . , TVN) in the anatomical body part; c) acquiring (S1.3), at the at least one processor, electric stimulation device geometry data describing a distance between the at least two contacts of the electric stimulation device (7); d) determining (S1.4), by the at least one processor and based on the target position data, target distance data describing a distance between each pair
(Continued)

of the at least two target regions; e) determining (S1.5), by the at least one processor and based on the target position data and the target distance data and the electric stimulation device geometry data, electric stimulation device position data describing a stimulation position which is a relative position between the at least two target regions (TV1, ..., TVN) and the electric stimulation device (7) which allows for stimulation of the at least two target regions (TV1, ..., TVN) by the electric stimulation device (7).

15 Claims, 12 Drawing Sheets

(56) References Cited

U.S. PATENT DOCUMENTS

| | | |
|---|---|---|
| 8,359,100 B2 | 1/2013 | Cameron et al. |
| 8,660,635 B2 | 2/2014 | Simon et al. |
| 9,289,144 B2 | 3/2016 | Lujan et al. |
| 2005/0267347 A1 | 12/2005 | Oster |
| 2008/0103547 A1 | 5/2008 | Okun et al. |
| 2012/0116211 A1 | 5/2012 | McIntyre et al. |
| 2015/0223777 A1* | 8/2015 | Rasoulian ............ A61B 8/4444 600/461 |

FOREIGN PATENT DOCUMENTS

| | | |
|---|---|---|
| WO | 2016019129 A1 | 2/2016 |
| WO | 2017028934 A1 | 2/2017 |
| WO | 2018157909 A1 | 9/2018 |

OTHER PUBLICATIONS

Miocinovic, Svjetlana et al., Experimental and theoretical characterization of the voltage distribution generated by deep brain stimulation, Experimental Neurology 2016, 166-176, Dec. 11, 2008.

* cited by examiner

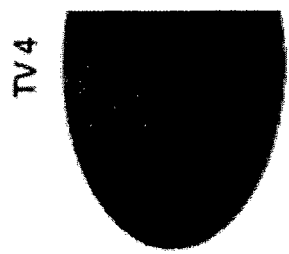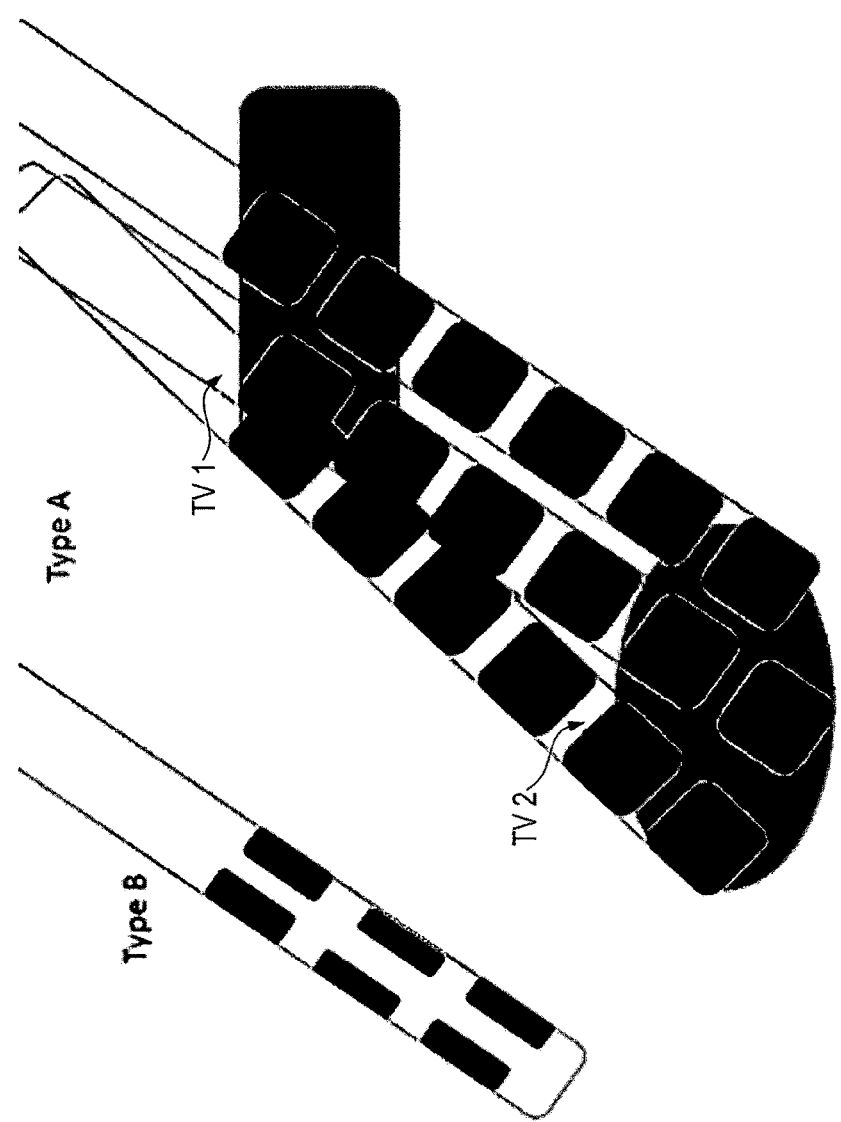
Fig. 9

OPTIMAL DEEP BRAIN STIMULATION ELECTRODE SELECTION AND PLACEMENT ON THE BASIS OF STIMULATION FIELD MODELLING

The present invention relates to a computer-implemented method for planning a position of an electric stimulation device for neurostimulation of at least two target regions disposed in an anatomical body part of a patient's body, the electric stimulation device comprising at least two electric contacts, a computer configured to execute a corresponding program and a medical system for planning a position of an electric stimulation device comprising such a computer.

TECHNICAL BACKGROUND

When areas of the brain are to be stimulated by deep brain stimulation (DBS)—these areas to be stimulated are known prior to the surgical implantation yet the stimulation capabilities of the device are seldom used to simulate optimal coverage of the target region and infer an optimized surgical trajectory for placement on the basis of this information or select the right device—various deep brain stimulation electrodes differ widely with respect to the tissue volume they can stimulate due to number of contacts, their span and their directionality capabilities. This is specifically relevant in cases where two or more areas are to be stimulated after a single pass implantation of a device. With this invention the trade-off between device selection and surgical flexibility in terms of chosen approaches in quantified to aid the user in making the optimal choice for the patient prior to surgery.

Previous solutions focussed merely on avoidance regions and did only use spherical stimulation fields, which allow for virtual 360 degrees of possible approach vectors/trajectories. With the advent of directional stimulation systems on the other hand, non-spherical stimulation fields can have a limited number of solutions that constitute valid and clinically realistic approach vectors. Ranking these in an anatomically useful manner and accounting for multi-target approaches are additions to the current art—specifically with an outlook towards anti-dromic and pro-dromic fiber stimulation.

The present invention is designed to provide a method and system for improved simulation of electric stimulation of an anatomical body part and selection of a suitable stimulation device.

Aspects of the present invention, examples and exemplary steps and their embodiments are disclosed in the following. Different exemplary features of the invention can be combined in accordance with the invention wherever technically expedient and feasible.

Exemplary Short Description of the Present Invention

In the following, a short description of the specific features of the present invention is given which shall not be understood to limit the invention only to the features or a combination of the features described in this section.

The disclosed method for planning an electrode position encompasses fitting the position and stimulation field characteristics of a stimulation electrode for e.g. deep brain stimulation to positions of a plurality of target regions and avoidance regions. To that end, information about the geometry of the electrode and the position of at least the envisaged target regions is combined determine a position of the electrode relative to all of the target regions which is suitable for stimulating all of the target regions at least to a predetermined degree. Furthermore, the position of the electrode may additionally be determined such that avoidance regions are avoided at least to a predetermined degree by at least one the trajectory of the electrode or the effects of the stimulating electric field to be emitted by the electrode. The disclosed method is a simulation method and does not encompass actual insertion of the electrode into any part of a patient's body or application of the stimulating electric field to any part of the patient's body.

General Description of the Present Invention

In this section, a description of the general features of the present invention is given for example by referring to possible embodiments of the invention.

In general, the invention reaches the aforementioned object by providing, in a first aspect, a computer-implemented medical method for planning a position of an electric stimulation device (for example, an electrode such as a multi-contact electrode) for neurostimulation of at least two target regions disposed in an anatomical body part of a patient's body. Notably, placement of such an electrode is not part of the disclosed method. Furthermore, execution of the disclosed method does not require the electrode to be placed while the disclosed method is executed. Rather, the method is for example a data processing method and comprises executing, on at least one processor of at least one computer (for example at least one computer being part of a deep brain stimulation calibration or tuning system), the following exemplary steps which are executed by the at least one processor.

In a (for example first) exemplary step, medical image data is acquired which describes (for example, representing or defining) a digital image of the anatomical body part. The anatomical body part contains for example at least two target regions. In a certain example, the anatomical body part contains exactly two target regions, and then the data processing conducted by executing the method according to the first aspect applies to exactly two target regions. In one example, each target region contains at least one nerve fibre, i.e. at least one nerve fibre runs through each target region. However, a target region (specifically, none of the target regions) may not contain any nerve fibre (for example, if the anatomical body part comprises a muscle as a target region which shall be stimulated). In further examples, the number of target regions considered by the method according to the first aspect is exactly three or more than three, exactly four or more than four, exactly five or more than five or exactly ten or more than ten. The medical image data may have been generated before execution of the disclosed method starts, but in one example of the disclosed method, generation of the medical image data is performed as a step of the disclosed method.

The imaging modality used for generating the medical image data is for example a tomographic imaging modality such as at least one of a computed x-ray tomography (CT), a magnetic resonance tomography (MR), a positron emission tomography (PET) or an ultrasound tomography (sonography). In a specific example, the imaging modality is diffusion-weighted magnetic resonance imaging (MRI) (generated for example by magnetic resonance diffusion tensor imaging—MR-DTI). In a general example, the medical image data is defined in three spatial dimensions and therefore constitutes three-dimensional image data. In that example, all data sets derived from the medical image data or the applied to the medical image data may also be defined in three spatial dimensions. Specifically, the below-described search region data (for example, the lattices/grids defined by the search may be defined in three spatial dimensions.

Generally, the anatomical body part may be any anatomical body part containing at least one nerve fibre which may be electromagnetically stimulated from the outside of the anatomical body part and for example runs close to the surface of the anatomical body part, but of course still within the anatomical body part. In a more specific example, the anatomical body part is at least part of the brain.

In a further (for example second) exemplary step, target position data describing (for example, representing or defining) a position of each target region in the anatomical body part is determined. The target position data is determined based on the medical image data. For example, the target position data is determined by defining, in the reference system in which positional information associated with the medical image data is defined (specifically, by defining in the medical image data), the position of each target region.

A specific example of this for example second exemplary steps encompasses acquiring atlas data describing (for example, representing or defining) an image-based model of the anatomical body part. In this specific example, the method comprises at least one of the following steps i) or ii):
  i) determining, based on the atlas data and the medical image data, the target position data;
  ii) determining, by the at least one processor and based on the atlas data and the medical image data, avoidance region data describing the position of at least one avoidance region in the anatomical body part which shall not be influenced by the stimulation.

Step i) can be implemented by establishing a transformation (for example, a positional transformation) between the reference systems in which positional information in the atlas data and the medical image data, respectively, is defined. Within this disclosure, a transformation is understood to be for example a linear mapping which may be represented by a multi-column matrix or a vector, which is established according to the known principles of linear algebra, for example between two reference systems (e.g. coordinate systems). One way of establishing such a transformation is by applying a fusion algorithm (such as an elastic or rigid fusion algorithm to (at least) two datasets which comprise information which is defined in each a positional reference system (coordinate system). The transformation between the atlas data and the medical image data can be established for example by comparing colour values (such as greyscale values) in both data sets and thereby associating image contents with one another which describes the same and/or anatomical structures in both data sets. Thereby, a potential difference in position of the respective image contents relative to the position of other image contents can be determined, and translation and/or rotation (for example, distortion) between the image contents of the two data sets can be determined. The transformation is then determined (for example, in an inverse manner) such that it defines such translation and/or rotation. After establishing the transformation between the medical image data and the atlas data, the transformation can be used for determining, outgoing from the position of the target region known in the reference system of the atlas data, the position of the target region in the reference system of the medical image data (i.e. in the medical image data) by applying the transformation (which may be defined in the direction from the reference system of the atlas data to the reference system of the medical image data, i.e. such that it transforms positions defined in the reference system of the atlas data into positions in the reference system of the medical image data) to the position of the target region in the reference system of the atlas data.

Step ii) can be implemented by establishing a transformation between the reference systems in which positional information in the atlas data and the medical image data, respectively, is defined, as described above with regard to step i). The transformation can be used for determining, outgoing from the position of the target region known in the reference system of the atlas data, the position of the avoidance region in the reference system of the medical image data (i.e. in the medical image data) by applying the transformation (which may be defined in the direction from the reference system of the atlas data to the reference system of the medical image data, i.e. such that it transforms positions defined in the reference system of the atlas data into positions in the reference system of the medical image data) to the position of the avoidance region in the reference system of the atlas data. An avoidance region is for example an organ at risk or at least part of an organ which shall not be influenced, for example not negatively affected, by the stimulation. An example of such a part of an organ is a specific functional region of the brain such as the respiratory centre or the speech centre.

The atlas data may describe a multimodal atlas of the anatomical body part in which models of the anatomical body parts are stored which have been generated with each a different imaging modality, and a transformation rule between anatomically corresponding parts of the models. That allows for a transformation of the medical image data into an imaging modality which is different from the one which was used for its generation, for example to make the medical image data comparable to that different imaging modality. The transformation rule may be based on tissue class information stored for each model which describes the image appearance (e.g. colour value such as a multi-colour value or a greyscale value) of the constituents of the anatomical body part in the respective imaging modality.

Furthermore, the atlas data may have been generated from medical images of the anatomical body part of a plurality of patients. Alternatively, the atlas data may have been generated from at least one medical image of the anatomical body part of only the specific patient for whom the medical image data was generated, i.e. the model may be part of a patient-specific atlas.

The atlas data comprises for example positional information defined in a three-dimensional coordinate system (representing the reference system used for defining positional information contained in the atlas data). For example, the atlas data has been generated from tomographic images of the anatomical body part. In one example, the atlas data contains positional information describing (for example, defining or representing) a relative position between the exterior part and the nerve fibre in the image-based model. For example, the atlas data contains information describing (for example, defining or representing) the position of the target region in the positional reference system (e.g. coordinate system) used for defining positions in the image-based model. From that information, the relative position between the position of the exterior part and the position of the nerve fibre can be calculated. The information about the position of each of the exterior part and the nerve fibre therefore also defines the relative position.

If the method comprises step i), the target position data may alternatively be determined by applying a statistical map of potential target positions in the image-based model described by the atlas data, or by applying a segmentation of the atlas data describing a position of at least one potential target region in the image-based model, to the medical image data. If the method comprises step ii), the avoidance region data may alternatively be determined by applying a statistical map of positions of potential avoidance regions in the image-based model described by the atlas data, or by applying a segmentation of the atlas data describing a position of at least one avoidance region in the image-based model, to the medical image data. A statistical map is a predetermined data set containing information about the statistical spatial distribution, in the anatomical body part, of envisaged target regions.

In a further (for example third) exemplary step, electric stimulation device geometry data is acquired which describe (for example, represents or defines) a distance between the at least two contacts of the electric stimulation device. The electric stimulation device geometry data is for example predetermined (i.e. at least one of fixed or known) and for example depends on the electric stimulation device to be used for the envisaged stimulation. The electric stimulation device geometry data may be embodied by a geometric template for a specific electric stimulation device which may be supplied for example by a manufacturer of the electric stimulation device. For example, the electric stimulation device is an electrode and the electric stimulation device geometry data describes (for example, represents or defines) a maximum distance (for example, along the longitudinal axis of an elongated electrode) between contacts of the electrode. For example, the distance is the distance (for example, along the longitudinal axis of the electrode, alternatively the direct distance between specified parts of the respective contacts) between the most distal contact (the contact closest to the tip—i.e. the patient-side end—of the electrode) and the most proximal contact (the contact most distant from the tip of the electrode). If the electric stimulation device is an elongate electrode, its shape may be approximated as being cylindrical, and its axis can then be defined as the trace of such a cylinder.

In a further (for example fourth) exemplary step, target distance data is determined which describes (for example, represents or defines) a distance between each pair of the at least two target regions. The target distance data is determined based on the target position data. For example, all possible pairings of each two of the at least two target regions are established, excluding duplicate pairings. Each pairing describes a pair of (exactly) two target regions. Then, a distance between the two target regions (for example, between their centre points such as centres of gravity, for example geometric centres of gravity) making up each pair is computed. The distance is computed from the positional information contained in the target position data, i.e. from the coordinates defining the position of each target region as described by the target position data.

The distance between the target regions is in one example calculated as the Hausdorff distance which describes the maximum positional deviation of two structures from one another and is defined as:

$$H(A, B) = \max\{h(A, B), h(B, A)\} \text{ with } h(A, B) = \max_{a \in A} \min_{b \in B} d(a, b) \quad (1)$$

where A is the set of all surface points of the comparison structure (one of the two target regions forming a pair) and B is the set of all surface points of the reference structure (the other one of the two target regions forming a pair) and d(a; b) is the distance of two surface points of A and B in the metric space of the real numbers with the usual metric induced by the absolute value $d=|a-b|$. In more general words, the distance is in this example calculated as the greatest of all distances from one point in set A to one point in set B.

In one specific example of this for example fourth exemplary step, the target distance data is determined further based on the electric stimulation device geometry data, for example by considering only a distance between the target regions which has a predetermined relationship to, for example is not larger than, the distance between the at least two contacts. For example, this way only target regions being distant from one another no further than the maximum distance between the two most distant contacts of an electrode used as a stimulating device can be selected as target regions for the stimulation to be planned. This helps to ensure that a planned electric filed to be generated between the positions of the contacts actually covers all target regions to be considered.

In a further (for example fifth) exemplary step, electric stimulation device position data is determined based on the target position data and the target distance data and the electric stimulation device geometry data. The electric stimulation device position data describes (for example, represents or defines) a stimulation position which is a relative position between the at least two target regions and the electric stimulation device which allows for stimulation of the at least two target regions by the electric stimulation device. Specifically, the stimulation position is determined such that the at least two target regions lie in an area which can be covered by an electric field emittable (for example, emitted) by the electric stimulation device. The area is determined such that the distance described by the target distance data electric stimulation device data and the information described by the electric stimulation device geometry data (for example, the maximum distance between electrodes) is fulfilled as a boundary condition. For example, the boundary condition is defined such that the distance from the position of the electric stimulation device to any point in one of the target regions is less than or equal to maximum distance between the electrodes. The relative position is determined for all target regions to be considered in total, i.e. for the set of target regions under examination, and not for each target region individually. In other words, the relative position is determined such that not only one or a real subset of the target regions and examination can be covered by the electric field, but such that all of the target regions under examination can be covered simultaneously (at least to a desired degree). For example, the extent of the electric field shall not be less than the maximum distance between the contacts while still covering the at least two target regions. For example, the stimulation position allows for stimulation of the at least two target regions by the at least two contacts. Ideally, each target region is to be stimulated by an individual electric field. The electric stimulation device position data can be determined by a iterative method for determining a suitable relative position between the at least two target regions, for example by keeping at least one of the relevant parameters (such as at least one of the position of the target regions or the strength and time behaviour of the electric field to be emitted by the electric stimulation device or the spatial extent of the electric field, determined for example by the maximum distance between electrodes, or the distribution of the electric field strength onto different contacts of an electrode as a electric stimulation device) constant and varying at least one other one of the relevant parameters (such as the position of the electric stimulation device) until the boundary conditions (for example, at least one simultaneous coverage of all target regions at least to a predetermined degree of at least one avoidance region at least to a predetermined degree) are fulfilled.

For example, the method according to the first aspect includes a step of determining, search region data which describes (for example, represents or defines) each one search region around the position of each one of the at least two target regions. The search region data is determined based on the target position data. The search region constitutes a maximum distance around each target volume which shall be searched for a suitable relative position of between the electric stimulation device and the respective target region. The extent of the search region can be defined for example by the maximum distance between contacts of the electrode, i.e. the search region data in one example is determined based on the electric stimulation device geometry data. The electric stimulation device position data can then be determined further based on the search region data. For example, the iterative method of determining the electric stimulation device position data is determined by searching one search region for a suitable relative position between the electric stimulation device and the target region associated with that search region. If such a relative position has been determined, the associated position of the electric stimulation device is fixed and a search region around another one of the at least two target regions is searched for a suitable relative position between the electric stimulation device and the other target region, considering for example an elongated (for example, linear) configuration of the electric stimulation device (such as a linear setup of electrodes along a longitudinal extension of an electrode as a electric stimulation device). For example, the position of one contact relative to the first target region is held fixed, and the direction in which the longitudinal extension points is varied until a desired coverage of the other target region with the desired electric field is achieved. This process can be repeated for an arbitrary number of target regions until an optimized coverage of the entire set of target regions under consideration is achieved. To this end, an optimization procedure can be additionally executed to determine whether any deviation from a desired coverage of at least one of the target regions or avoidance of an avoidance region under consideration is acceptable, considering the coverage thereby achievable for the other target regions (applying at least one of for example an individual boundary condition for the acceptability of the coverage for each target region, or for the target regions in total, or an individual boundary condition for the acceptability of the avoidance of each avoidance region, or for a plurality of (i.e. at least two) avoidance regions in total).

For example, the search regions are defined by lattices (grids) having lattice (grid) points and the longitudinal extension of the electric stimulation device is positioned on one of the lattice points in a first search region. This position is the kept fixed, and the longitudinal position of the stimulation is placed such that another point of the electric stimulation device is positioned on one of the lattice points of a lattice associated with a second, other search region. This procedure can be repeated for the entire set of search regions, wherein the position of the electric stimulation device on the lattice point of the first search region can either be kept fixed as a boundary condition for determining the other applicable lattice points onto which the electric stimulation device shall be placed in the other search regions or can be varied so that lattice point in the first search region onto which the electric stimulation device is placed may also vary during the iterative procedure until at least one of an optimal coverage of all target regions or avoidance of avoidance regions has been achieved according to the applicable boundary conditions. For example, this above procedure comprises determining the electric stimulation device position data by determining a plurality of trajectories which run through a lattice point of the search region associated with a first one of the at least two target regions, and run through a lattice point of the search region associated with a second (other) one of the at least two target regions. In on example, the trajectories are straight line trajectories which resemble the geometry of an elongate electric stimulation device (such as a linear electrode). The stimulation position may then be determined by selecting, from the plurality of trajectories, one optimal trajectory which may serve as a trajectory for inserting the electric stimulation device in the anatomical body part so that at least one of the coverage of the at least two target regions for stimulation by the electric stimulation device or avoidance of avoidance regions is optimal considering the distance between the at least two contacts. For example, the method according to the first aspect may comprise above-mentioned step ii), and the optimal trajectory may then be selected if it has a predetermined spatial relationship relative to, for example does not intersect or has a minimum distance from, an avoidance region in the anatomical body part which shall not be influenced by the stimulation.

In a second aspect, the invention is directed to a computer program which, when running on at least one processor (for example, a processor) of at least one computer (for example, a computer) or when loaded into at least one memory (for example, a memory) of at least one computer (for example, a computer), causes the at least one computer to perform the above-described method according to the first aspect.

In a third aspect, the invention is directed to a non-transitory computer-readable program storage medium on which the program according to the fourth aspect is stored.

In a fourth aspect, the invention is directed to at least one computer (for example, a computer), comprising at least one processor (for example, a processor) and at least one memory (for example, a memory), wherein the program according to the fourth aspect is running on the processor or is loaded into the memory, or wherein the at least one computer is operably coupled to the program storage medium according to the fifth aspect for executing the program stored on the program storage medium.

In a seventh aspect, the invention is directed to a (physical, for example electrical, for example technically generated) signal wave, for example a digital signal wave, carrying information which represents the program according to the second aspect.

In an eighth aspect, the invention is directed to a medical system for planning a position of an electric stimulation device, the system comprising:
  a) the at least one computer according to the fourth aspect; and
  b) at least one electronic data storage device storing at least one of the medical image data or the electric stimulation device geometry data or the atlas data, wherein the at least one computer is operably coupled to the at least one electronic data storage device for acquiring, from the at least one data storage device, at least one of the medical image data or the electric stimulation device geometry data or the atlas data.

The system according to the eighth aspect in one example further comprises:
the electric stimulation device, wherein
the electric stimulation device is operably coupled to the at least one computer for navigation of the electric stimulation device to the stimulation position.

The system according to the eighth aspect may in a further example comprise a calibration apparatus for determining whether the electric stimulation device has been appropriately placed in the anatomical body part on the basis of (i.e. in accordance with) the electric stimulation device position data. For example, the correct position may be determined by image-based verification by taking a (for example digital) medical image (e.g. a radiography or a computed x-ray tomography) of the electric stimulation device being implanted in the anatomical body part which may serve as a basis for comparison with the electric stimulation device position data. Provided spatial relationship between the positional reference system of the medical image and the positional reference system of the electric stimulation device position data is known, the electric stimulation device position described by both can be compared. If the comparison results that the electric stimulation device position is for example at least to a predetermined degree similar (for example, equal), it can then be determined that the electric stimulation device has been placed in the anatomical body part as desired. Alternatively or additionally, it can be determined whether the electric stimulation device stimulates the target regions as desired by for example transcranial magnetic stimulation. For such a procedure, the system may comprise an a measurement device such an induction device comprising an induction coil which is placed to the exterior of the anatomical body part where for example an external (sub-body surface) end of a nerve fibre running through a target region runs. Then, the respective target region is stimulated by appropriately activating the electric stimulation device. If the induction device then receives an (alternating) electric signal from the anatomical body part, a measurable induction current in the induction device will show this. If such a current is measured, it can then be determined that the electric stimulation device has been placed in the anatomical body part as desired. The position at which the measurement device should be placed for such a procedure can be determined for example from the atlas data if the atlas data comprises information about the position of the respective end of the nerve fibre. The measurement device may also be navigated, for example be provided with at least one optical tracking marker for tracking its position using an optical navigation system (having a tracking unit, for example a stereo camera for tracking the at least one marker device, and outputting a corresponding electric signal convertible into digital data). Such a navigation system comprises a computer which evaluates the signals outputted by the tracking unit and on their basis calculates the position of the measurement device in an associated positional reference system. Assuming that the spatial relationship between the positional reference system of the navigation system and the positional reference system of the atlas data is known, it can be determined whether the measurement device has been appropriately placed relative to the nerve fibre.

Generally, it will be desired that application of the applied stimulation signal by the electric stimulation device stimulates a predetermined (at least one of known or desired) nerve fibre. Actually placing the induction coil is not necessarily part of the disclosed method, but may be a part of it. The disclosed method in any case encompasses reading the measurement data received from the measurement device which may be stored in an electronic data storage device and read by the disclosed method sometime after the measurement data was taken. The position at which the electric stimulation device needs to be positioned relative to the exterior part so as to stimulate the exterior part is determined for example using a navigation system. For example, a marker device is attached to the electric stimulation device in a predetermined (at least one of known or fixed) relative position. The marker device is suitable for optically navigating the position of the electric stimulation device by using a stereotactic navigation system which also knows the position of the exterior region in the reference system used for the optical navigation, for example from predetermined positional information included in the medical image data. Thus, the electric stimulation device can be navigated to a position relative to the exterior part which is suitable for stimulation of the exterior part by the electric stimulation device.

The emitted stimulation signal generally is a time-dependent electric signal such as an alternating current and/or an alternating electromagnetic field. If the measurement device (e.g. the induction coil) is placed in such an electromagnetic field, this will induce a measurement current in the induction coil which has physical properties (such as frequency) which allow comparing it to the corresponding known properties described by the stimulation signal data. This allows detecting whether the predetermined nerve fibre has been stimulated: if the measurement device is placed over an exterior part known to be connected to the predetermined nerve fibre, and if applying the applied stimulation signal leads to detection of a corresponding (comparable) emitted stimulation signal in the proximity of the nerve fibre, it will be justified to assume that the predetermined nerve fibre has been stimulated with the applied stimulation signal and that the electrode measuring the emitted stimulation signal was placed correctly relative to the position of the predetermined nerve fibre when applying the applied stimulation signal. It can then be further assumed that that position of the electrode is also suitable for using the electrode to stimulate the nerve fibre. If no emitted stimulation signal is detected, it will be justified to assume that the predetermined nerve fibre was not stimulated despite application of the applied stimulation signal by the electric stimulation device. This will be an indicator that the electrode for detecting the emitted stimulation signal was not placed correctly relative to the position of the predetermined nerve fibre when applying the applied stimulation signal. It can then be further assumed that that position of the electrode is not suitable for using the electrode to stimulate the nerve fibre. This procedure therefore allows finding a position of the electrode suitable for deep brain stimulation via the electrode.

In general, the invention does not involve or for example comprise or encompass an invasive step which would represent a substantial physical interference with the body requiring professional medical expertise to be carried out and entailing a substantial health risk even when carried out with the required professional care and expertise. For example, the invention does not comprise a step of irradiating the anatomical body part and/or the patient's body with ionizing radiation so that it does not comprise any steps of therapy of the human or animal body, for example it does not comprise any step of therapy or surgery. More particularly, the invention does not involve or in particular comprise or encompass any surgical or therapeutic activity. The invention is instead directed as applicable to reading data corresponding to an electric signal applied to a nerve fibre (the applied stimulation signal) and emitted from an exterior part (the emitted stimulation signal) which has an electrically conducting connection to the nerve fibre. For this reason alone, no surgical or therapeutic activity and in particular no surgical or therapeutic step is necessitated or implied by carrying out the invention.

It is within the scope of the present invention to combine one or more features of one or more embodiments or aspects of the invention in order to form a new embodiment wherever this is technically expedient and/or feasible. Specifically, a feature of one embodiment which has the same or a similar function to another feature of another embodiment can be exchanged with said other feature, and a feature of one embodiment which adds an additional function to another embodiment can for example be added to said other embodiment.

Definitions

In this section, definitions for specific terminology used in this disclosure are offered which also form part of the present disclosure.

The method in accordance with the invention is for example a computer implemented method. For example, all the steps or merely some of the steps (i.e. less than the total number of steps) of the method in accordance with the invention can be executed by a computer (for example, at least one computer). An embodiment of the computer implemented method is a use of the computer for performing a data processing method. An embodiment of the computer implemented method is a method concerning the operation of the computer such that the computer is operated to perform one, more or all steps of the method.

The computer for example comprises at least one processor and for example at least one memory in order to (technically) process the data, for example electronically and/or optically. The processor being for example made of a substance or composition which is a semiconductor, for example at least partly n- and/or p-doped semiconductor, for example at least one of II-, III-, IV-, V-, VI-semiconductor material, for example (doped) silicon and/or gallium arsenide. The calculating steps described are for example performed by a computer. Determining steps or calculating steps are for example steps of determining data within the framework of the technical method, for example within the framework of a program. A computer is for example any kind of data processing device, for example electronic data processing device. A computer can be a device which is generally thought of as such, for example desktop PCs, notebooks, netbooks, etc., but can also be any programmable apparatus, such as for example a mobile phone or an embedded processor. A computer can for example comprise a system (network) of "sub-computers", wherein each sub-computer represents a computer in its own right. The term "computer" includes a cloud computer, for example a cloud server. The term "cloud computer" includes a cloud computer system which for example comprises a system of at least one cloud computer and for example a plurality of operatively interconnected cloud computers such as a server farm. Such a cloud computer is preferably connected to a wide area network such as the world wide web (WWW) and located in a so-called cloud of computers which are all connected to the world wide web. Such an infrastructure is used for "cloud computing", which describes computation, software, data access and storage services which do not require the end user to know the physical location and/or configuration of the computer delivering a specific service. For example, the term "cloud" is used in this respect as a metaphor for the Internet (world wide web). For example, the cloud provides computing infrastructure as a service (IaaS). The cloud computer can function as a virtual host for an operating system and/or data processing application which is used to execute the method of the invention. The cloud computer is for example an elastic compute cloud (EC2) as provided by Amazon Web Services™. A computer for example comprises interfaces in order to receive or output data and/or perform an analogue-to-digital conversion. The data are for example data which represent physical properties and/or which are generated from technical signals. The technical signals are for example generated by means of (technical) detection devices (such as for example devices for detecting marker devices) and/or (technical) analytical devices (such as for example devices for performing (medical) imaging methods), wherein the technical signals are for example electrical or optical signals. The technical signals for example represent the data received or outputted by the computer. The computer is preferably operatively coupled to a display device which allows information outputted by the computer to be displayed, for example to a user. One example of a display device is an augmented reality device (also referred to as augmented reality glasses) which can be used as "goggles" for navigating. A specific example of such augmented reality glasses is Google Glass (a trademark of Google, Inc.). An augmented reality device can be used both to input information into the computer by user interaction and to display information outputted by the computer. Another example of a display device would be a standard computer monitor comprising for example a liquid crystal display operatively coupled to the computer for receiving display control data from the computer for generating signals used to display image information content on the display device. A specific embodiment of such a computer monitor is a digital lightbox. The monitor may also be the monitor of a portable, for example handheld, device such as a smart phone or personal digital assistant or digital media player.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, for example computer-readable data storage medium comprising computer-usable, for example computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, for example a data processing device comprising a digital processor (central processing unit or CPU) which executes the computer program elements, and optionally a volatile memory (for example a random access memory or RAM) for storing data used for and/or produced by executing the computer program elements. Within the framework of the present invention, a computer-usable, for example computer-readable data storage medium can be any data storage medium which can include, store, communicate, propagate or transport the program for use on or in connection with the instruction-executing system, apparatus or device. The computer-usable, for example computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. The data storage medium is preferably a non-volatile data storage medium. The computer program product and any software and/or hardware described here form the various means for performing the functions of the invention in the example embodiments. The computer and/or data processing device can for example include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or a vibration element incorporated into an instrument). For the purpose of this document, a computer is a technical computer which for example comprises technical, for example tangible components, for example mechanical and/or electronic components. Any device mentioned as such in this document is a technical and for example tangible device.

The expression "acquiring data" for example encompasses (within the framework of a The expression "acquiring data" for example encompasses (within the framework of a computer implemented method) the scenario in which the data are determined by the computer implemented method or program. Determining data for example encompasses measuring physical quantities and transforming the measured values into data, for example digital data, and/or computing the data by means of a computer and for example within the framework of the method in accordance with the invention. The meaning of "acquiring data" also for example encompasses the scenario in which the data are received or retrieved by the computer implemented method or program, for example from another program, a previous method step or a data storage medium, for example for further processing by the computer implemented method or program. Generation of the data to be acquired may but need not be part of the method in accordance with the invention. The expression "acquiring data" can therefore also for example mean waiting to receive data and/or receiving the data. The received data can for example be inputted via an interface. The expression "acquiring data" can also mean that the computer implemented method or program performs steps in order to (actively) receive or retrieve the data from a data source, for instance a data storage medium (such as for example a ROM, RAM, database, hard drive, etc.), or via the interface (for instance, from another computer or a network). The data acquired by the disclosed method or device, respectively, may be acquired from a database located in a data storage device which is operably to a computer for data transfer between the database and the computer, for example from the database to the computer. The computer acquires the data for use as an input for steps of determining data. The determined data can be output again to the same or another database to be stored for later use. The database or database used for implementing the disclosed method can be located on network data storage device or a network server (for example, a cloud data storage device or a cloud server) or a local data storage device (such as a mass storage device operably connected to at least one computer executing the disclosed method). The data can be made "ready for use" by performing an additional step before the acquiring step. In accordance with this additional step, the data are generated in order to be acquired. The data are for example detected or captured (for example by an analytical device). Alternatively or additionally, the data are inputted in accordance with the additional step, for instance via interfaces. The data generated can for example be inputted (for instance into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. The step of "acquiring data" can therefore also involve commanding a device to obtain and/or provide the data to be acquired. In particular, the acquiring step does not involve an invasive step which would represent a substantial physical interference with the body, requiring professional medical expertise to be carried out and entailing a substantial health risk even when carried out with the required professional care and expertise. In particular, the step of acquiring data, for example determining data, does not involve a surgical step and in particular does not involve a step of treating a human or animal body using surgery or therapy. In order to distinguish the different data used by the present method, the data are denoted (i.e. referred to) as "XY data" and the like and are defined in terms of the information which they describe, which is then preferably referred to as "XY information" and the like.

In the field of medicine, imaging methods (also called imaging modalities and/or medical imaging modalities) are used to generate image data (for example, two-dimensional or three-dimensional image data) of anatomical structures (such as soft tissues, bones, organs, etc.) of the human body. The term "medical imaging methods" is understood to mean (advantageously apparatus-based) imaging methods (for example so-called medical imaging modalities and/or radiological imaging methods) such as for instance computed tomography (CT) and cone beam computed tomography (CBCT, such as volumetric CBCT), x-ray tomography, magnetic resonance tomography (MRT or MRI), conventional x-ray, sonography and/or ultrasound examinations, and positron emission tomography. For example, the medical imaging methods are performed by the analytical devices. Examples for medical imaging modalities applied by medical imaging methods are: X-ray radiography, magnetic resonance imaging, medical ultrasonography or ultrasound, endoscopy, elastography, tactile imaging, thermography, medical photography and nuclear medicine functional imaging techniques as positron emission tomography (PET) and Single-photon emission computed tomography (SPECT), as mentioned by Wikipedia. The image data thus generated is also termed "medical imaging data". Analytical devices for example are used to generate the image data in apparatus-based imaging methods. The imaging methods are for example used for medical diagnostics, to analyse the anatomical body in order to generate images which are described by the image data. The imaging methods are also for example used to detect pathological changes in the human body. However, some of the changes in the anatomical structure, such as the pathological changes in the structures (tissue), may not be detectable and for example may not be visible in the images generated by the imaging methods. A tumour represents an example of a change in an anatomical structure. If the tumour grows, it may then be said to represent an expanded anatomical structure. This expanded anatomical structure may not be detectable; for example, only a part of the expanded anatomical structure may be detectable. Primary/high-grade brain tumours are for example usually visible on MRI scans when contrast agents are used to infiltrate the tumour. MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and for example discernible in the image generated by the imaging method. In addition to these tumours, referred to as "enhancing" tumours, it is thought that approximately 10% of brain tumours are not discernible on a scan and are for example not visible to a user looking at the images generated by the imaging method.

Image fusion can be elastic image fusion or rigid image fusion. In the case of rigid image fusion, the relative position between the pixels of a 2D image and/or voxels of a 3D image is fixed, while in the case of elastic image fusion, the relative positions are allowed to change.

In this application, the term "image morphing" is also used as an alternative to the term "elastic image fusion", but with the same meaning.

Elastic fusion transformations (for example, elastic image fusion transformations) are for example designed to enable a seamless transition from one dataset (for example a first dataset such as for example a first image) to another dataset (for example a second dataset such as for example a second image). The transformation is for example designed such that one of the first and second datasets (images) is deformed, for example in such a way that corresponding structures (for example, corresponding image elements) are arranged at the same position as in the other of the first and second images. The deformed (transformed) image which is transformed from one of the first and second images is for example as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are for example vectors of a deformation field. These vectors are determined by the optimisation algorithm in such a way as to result in an optimum degree of similarity. Thus, the optimum degree of similarity represents a condition, for example a constraint, for the optimisation algorithm. The bases of the vectors lie for example at voxel positions of one of the first and second images which is to be transformed, and the tips of the vectors lie at the corresponding voxel positions in the transformed image. A plurality of these vectors is preferably provided, for instance more than twenty or a hundred or a thousand or ten thousand, etc. Preferably, there are (other) constraints on the transformation (deformation), for example in order to avoid pathological deformations (for instance, all the voxels being shifted to the same position by the transformation). These constraints include for example the constraint that the transformation is regular, which for example means that a Jacobian determinant calculated from a matrix of the deformation field (for example, the vector field) is larger than zero, and also the constraint that the transformed (deformed) image is not self-intersecting and for example that the transformed (deformed) image does not comprise faults and/or ruptures. The constraints include for example the constraint that if a regular grid is transformed simultaneously with the image and in a corresponding manner, the grid is not allowed to interfold at any of its locations. The optimising problem is for example solved iteratively, for example by means of an optimisation algorithm which is for example a first-order optimisation algorithm, such as a gradient descent algorithm. Other examples of optimisation algorithms include optimisation algorithms which do not use derivations, such as the downhill simplex algorithm, or algorithms which use higher-order derivatives such as Newton-like algorithms. The optimisation algorithm preferably performs a local optimisation. If there is a plurality of local optima, global algorithms such as simulated annealing or generic algorithms can be used. In the case of linear optimisation problems, the simplex method can for instance be used.

In the steps of the optimisation algorithms, the voxels are for example shifted by a magnitude in a direction such that the degree of similarity is increased. This magnitude is preferably less than a predefined limit, for instance less than one tenth or one hundredth or one thousandth of the diameter of the image, and for example about equal to or less than the distance between neighbouring voxels. Large deformations can be implemented, for example due to a high number of (iteration) steps.

The determined elastic fusion transformation can for example be used to determine a degree of similarity (or similarity measure, see above) between the first and second datasets (first and second images). To this end, the deviation between the elastic fusion transformation and an identity transformation is determined. The degree of deviation can for instance be calculated by determining the difference between the determinant of the elastic fusion transformation and the identity transformation. The higher the deviation, the lower the similarity, hence the degree of deviation can be used to determine a measure of similarity.

A measure of similarity can for example be determined on the basis of a determined correlation between the first and second datasets.

Preferably, atlas data is acquired which describes (for example defines, more particularly represents and/or is) a general three-dimensional shape of the anatomical body part. The atlas data therefore represents an atlas of the anatomical body part. An atlas typically consists of a plurality of generic models of objects, wherein the generic models of the objects together form a complex structure. For example, the atlas constitutes a statistical model of a patient's body (for example, a part of the body) which has been generated from anatomic information gathered from a plurality of human bodies, for example from medical image data containing images of such human bodies. In principle, the atlas data therefore represents the result of a statistical analysis of such medical image data for a plurality of human bodies. This result can be output as an image—the atlas data therefore contains or is comparable to medical image data. Such a comparison can be carried out for example by applying an image fusion algorithm which conducts an image fusion between the atlas data and the medical image data. The result of the comparison can be a measure of similarity between the atlas data and the medical image data. The atlas data comprises positional information which can be matched (for example by applying an elastic or rigid image fusion algorithm) for example to positional information contained in medical image data so as to for example compare the atlas data to the medical image data in order to determine the position of anatomical structures in the medical image data which correspond to anatomical structures defined by the atlas data.

The human bodies, the anatomy of which serves as an input for generating the atlas data, advantageously share a common feature such as at least one of gender, age, ethnicity, body measurements (e.g. size and/or mass) and pathologic state. The anatomic information describes for example the anatomy of the human bodies and is extracted for example from medical image information about the human bodies. The atlas of a femur, for example, can comprise the head, the neck, the body, the greater trochanter, the lesser trochanter and the lower extremity as objects which together make up the complete structure. The atlas of a brain, for example, can comprise the telencephalon, the cerebellum, the diencephalon, the pons, the mesencephalon and the medulla as the objects which together make up the complex structure. One application of such an atlas is in the segmentation of medical images, in which the atlas is matched to medical image data, and the image data are compared with the matched atlas in order to assign a point (a pixel or voxel) of the image data to an object of the matched atlas, thereby segmenting the image data into objects.

It is the function of a marker to be detected by a marker detection device (for example, a camera or an ultrasound receiver or analytical devices such as CT or MRI devices) in such a way that its spatial position (i.e. its spatial location and/or alignment) can be ascertained. The detection device is for example part of a computer-based navigation system and can be a stereotactic camera which is sensitive to electromagnetic waves in a predetermined wavelength range such as the infrared wavelength range or any other wavelength range with which the marker are irradiated and which is reflected by the marker. The markers can be active markers. An active marker can for example emit electromagnetic radiation and/or waves which can be in the infrared, visible and/or ultraviolet spectral range. A marker can also however be passive, i.e. can for example reflect electromagnetic radiation in the infrared, visible and/or ultraviolet spectral range or can block x-ray radiation. To this end, the marker can be provided with a surface which has corresponding reflective properties or can be made of metal in order to block the x-ray radiation. It is also possible for a marker to reflect and/or emit electromagnetic radiation and/or waves in the radio frequency range or at ultrasound wavelengths. A marker preferably has a spherical and/or spheroid shape and can therefore be referred to as a marker sphere; markers can however also exhibit a cornered, for example cubic, shape.

A marker device can for example be a reference star or a pointer or a single marker or a plurality of (individual) markers which are then preferably in a predetermined spatial relationship. A marker device comprises one, two, three or more markers, wherein two or more such markers are in a predetermined spatial relationship. This predetermined spatial relationship is for example known to a navigation system and is for example stored in a computer of the navigation system.

In another embodiment, a marker device comprises an optical pattern, for example on a two-dimensional surface. The optical pattern might comprise a plurality of geometric shapes like circles, rectangles and/or triangles. The optical pattern can be identified in an image captured by a camera, and the position of the marker device relative to the camera can be determined from the size of the pattern in the image, the orientation of the pattern in the image and the distortion of the pattern in the image. This allows to determine the relative position in up to three rotational dimensions and up to three translational dimensions from a single two-dimensional image.

The position of a marker device can be ascertained, for example by a medical navigation system. If the marker device is attached to an object, such as a bone or a medical instrument, the position of the object can be determined from the position of the marker device and the relative position between the marker device and the object. Determining this relative position is also referred to as registering the marker device and the object. The marker device or the object can be tracked, which means that the position of the marker device or the object is ascertained twice or more over time.

DESCRIPTION OF THE FIGURES

In the following, the invention is described with reference to the appended figures which represent a specific embodiment of the invention. The scope of the invention is however not limited to the specific features disclosed in the context of the figures, wherein

FIGS. 2 to 11 illustrate the details of steps of the method according to the first aspect.

FIG. 1 is a flow diagram illustrating the basic steps of the disclosed method in accordance with the first aspect, which in the illustrative example of FIG. 1 starts with a step S1.1 of acquiring the medical image data. In subsequent step S1.2, the target position data is determined. Step S1.3 then continues with acquiring the electric stimulation device geometry data, followed by step S1.4 which encompasses determining the target distance data. Finally, step S1.6 is executed which comprises determining the electric stimulation device position data.

The following is a description of a more specific embodiment of the method in accordance with the first aspect with reference to FIGS. 2 to 11 and including the following step 1 to 17.

Figure 1:
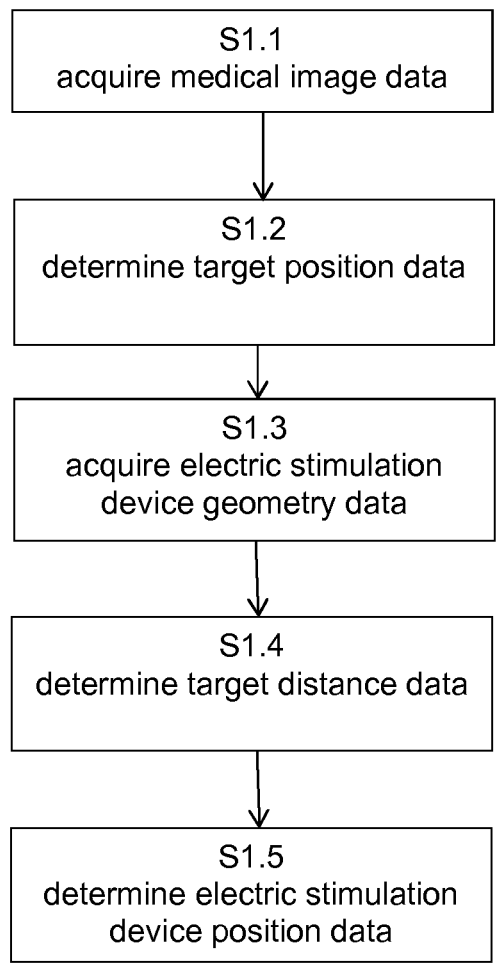
FIG. 1 is a flow diagram showing the basic steps of the disclosed method according to the first aspect.
Figure 2:
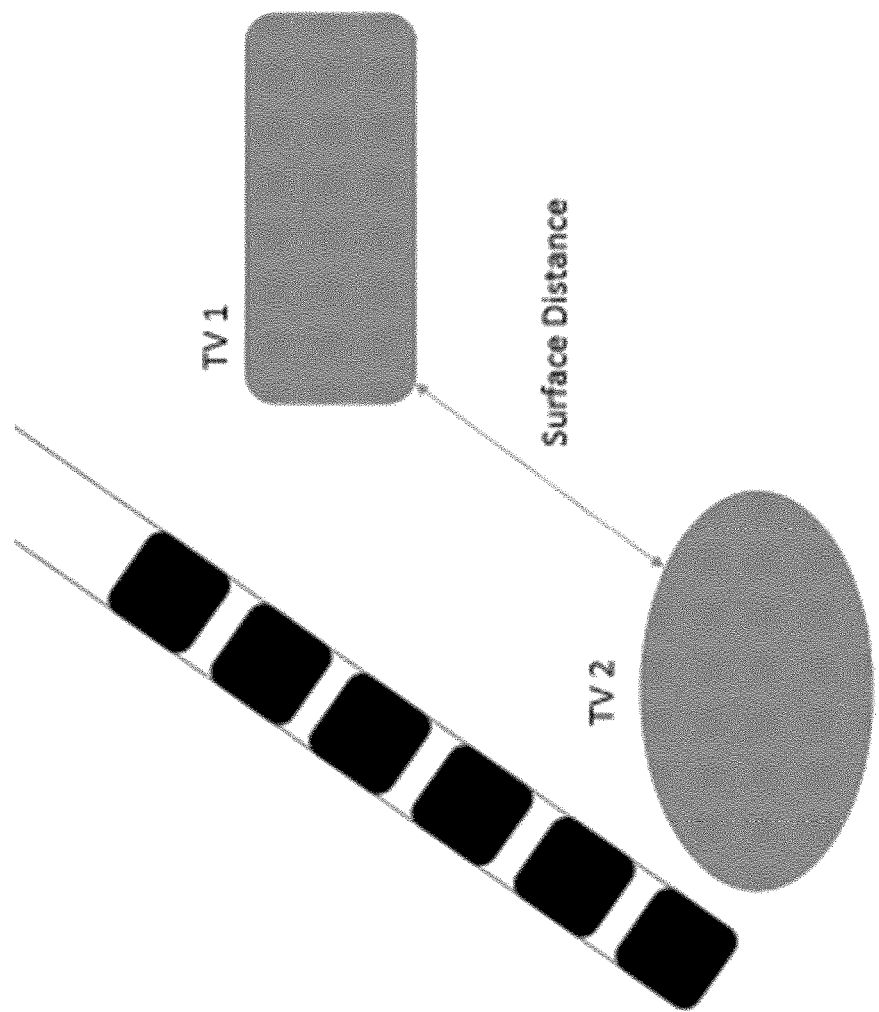

Steps 1 to 4 are explained with reference to FIG. 2.

Step 1:

Receive stimulation target fields representing the target regions TV1, . . . , TVN based on user input or from a statistical map (brought from Universal Atlas space) or via segmentation selection (segmentation based on Universal Atlas) on the medical image data (which has been acquired beforehand). This step corresponds to acquiring the target position data.

Example: left and right subthalamic nucleus STN (0.15 mm$^3$) and part of left and right SN (substantia nigra) (0.05 mm$^3$) drawn into the medical image data Step 2:

Receive avoidance field(s) AV1, . . . , AVN representing the avoidance regions based on user input or from a statistical map (brought from Universal Atlas space) or via segmentation selection (segmentation based on Universal Atlas). This step corresponds to determining the avoidance region data.

Example: sulcus segmentation volume, ventricle segmentation volume, vessel segmentation object Step 3:

Inflate all avoidance fields by a safety margin of X (e.g. 2 mm) based on user input—this step is entirely optional.

Step 4:

Calculate surface distances (Hausdorff distance) between TV1, . . . , TVN resulting in the stimulation target field surface distance matrix which is symmetric having N×N entries, wherein each entry describes the distance between two target volumes.

EXAMPLE

|  | left STN | right STN | left SN | right SN |
|---|---|---|---|---|
| left STN | X | 400 mm | 3 mm | 423 mm |
| right STN |  | X | 416 mm | 5 mm |
| left SN |  |  | X | 410 mm |
| right SN |  |  |  | X |

Figure 3:
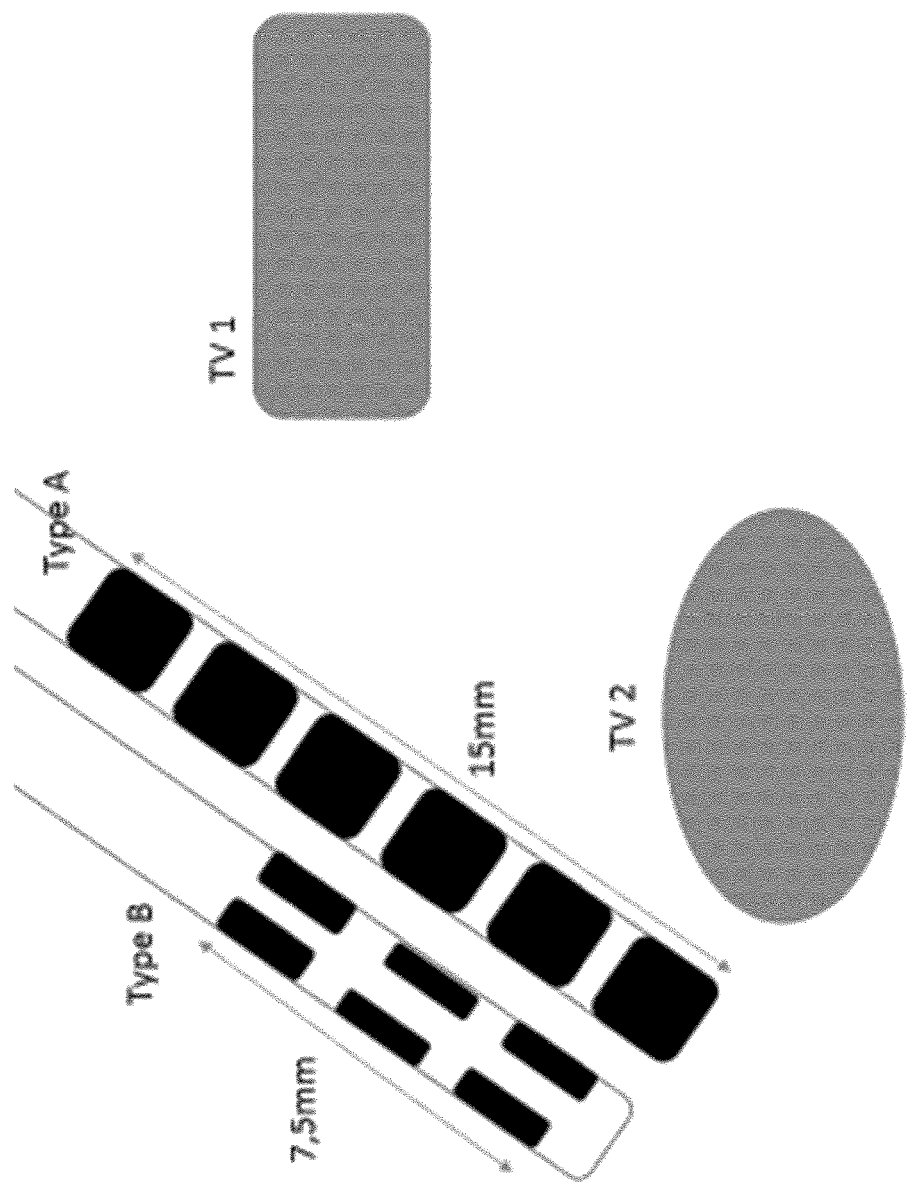
Figure 4:
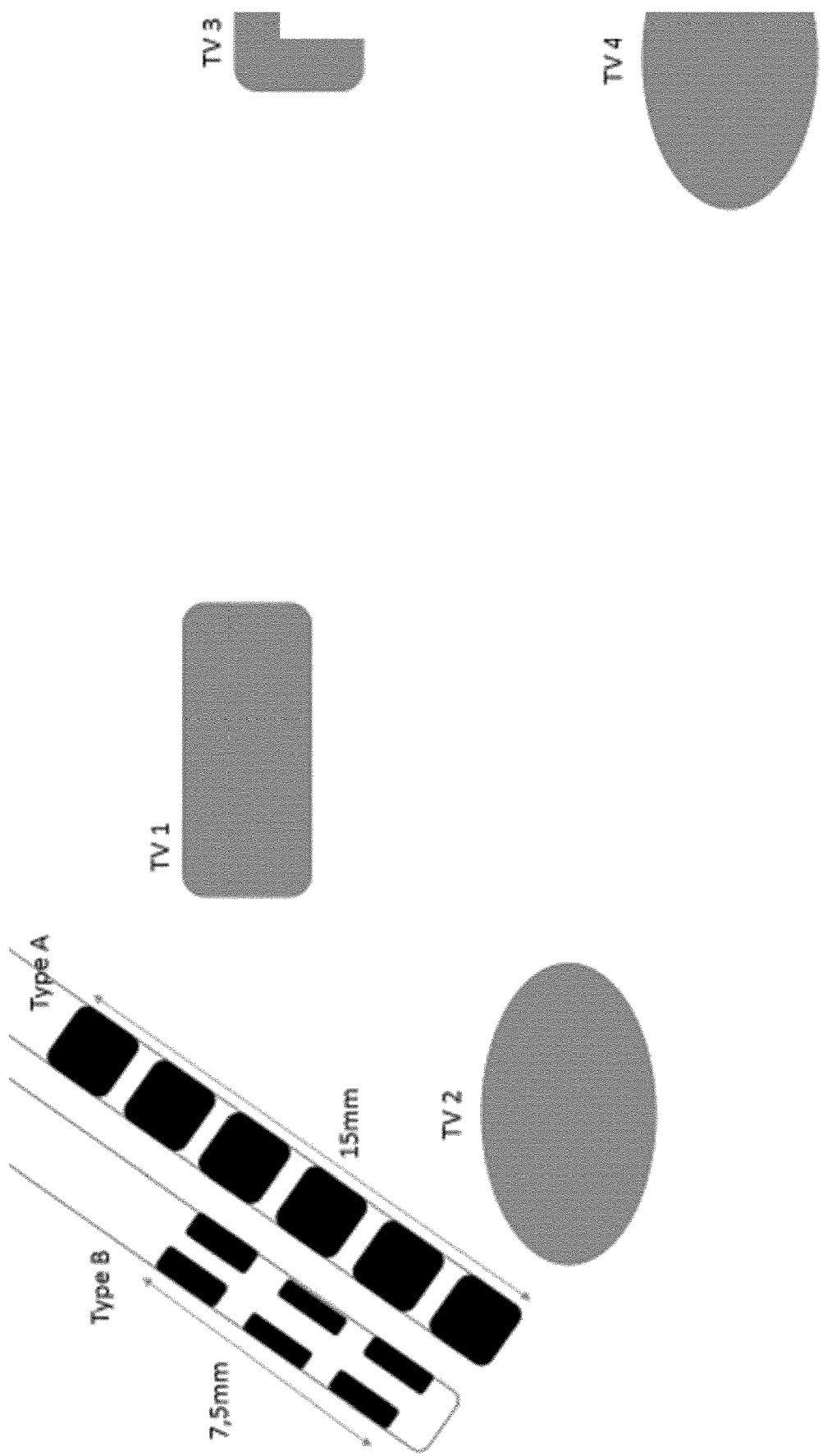

Step 5 is explained with reference to FIG. 3.

Step 5:

Load template list of available electrode types—this step corresponds to acquiring the electric stimulation device geometry data, and may be executed based on user input.

Example: Available Electrode Types are 1. linear lead: most proximal to most distal contact distance is 15 mm
2. directional lead: Most proximal to most distal contact distance is 7.5 mm Step 6 is explained with reference to FIG. 4

Step 6:

Search surface distance matrix for surface distances smaller than the maximal electrode contact distance for each template entry (penetration model, in one preferred alternative embodiment it is sufficient if the contacts can touch one or both target regions without having to necessarily penetrate the segmentation structure, i.e. the segmented target volume; this is due to the fact that the electrical field can extend below and above the contact in question with sufficient field size/strength). This steps corresponds to determining the target distance data.

Example

|  | left STN | right STN | left SN | right SN |
|---|---|---|---|---|
| left STN | X | N/A | L or D | N/A |
| right STN |  | X | N/A | L or D |
| left SN |  |  | X | N/A |
| right SN |  |  |  | X |

Figure 5:
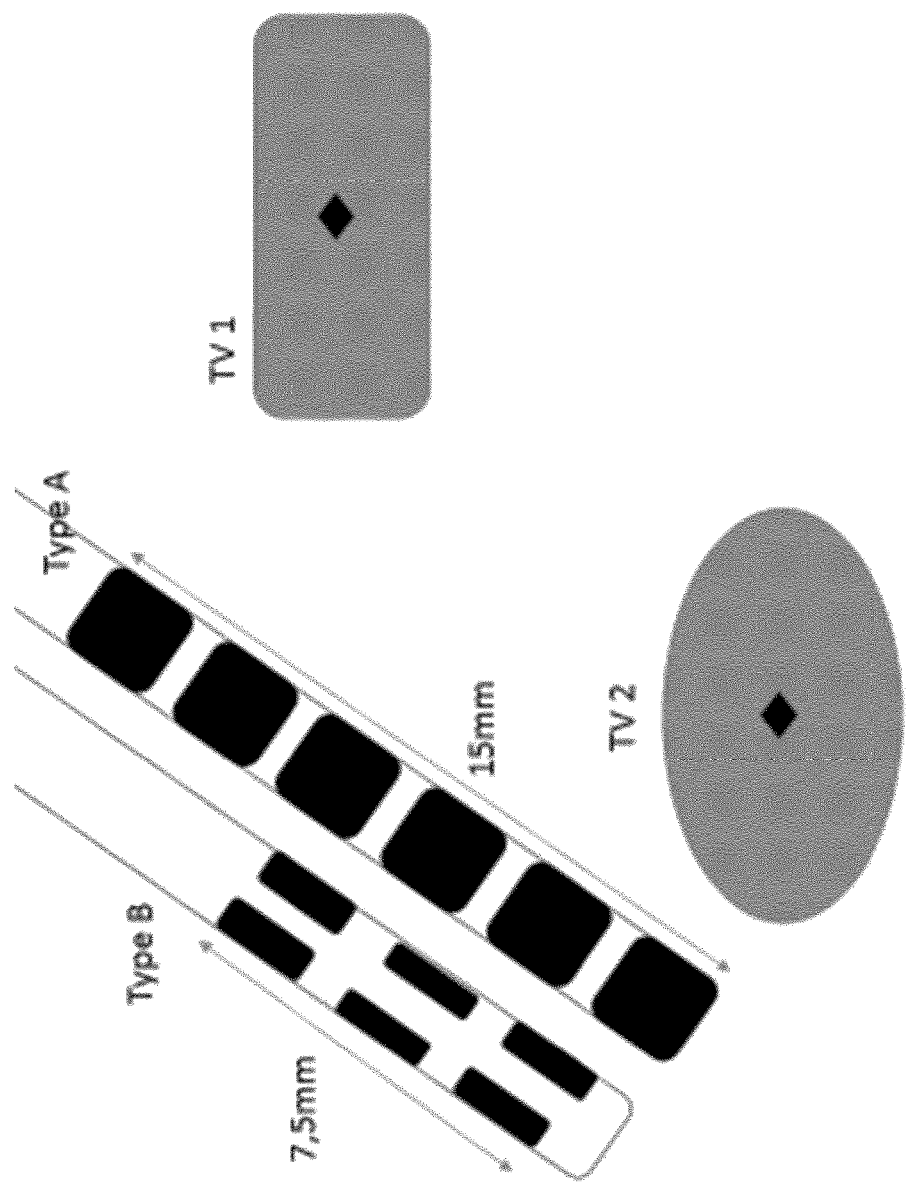

Steps 7 to 9 are explained with reference to FIG. 5. FIG. 5 shows two types of electrodes, namely an electrode of type A (linear lead electrode) and an electrode of type B (directional lead electrode). The contacts of the electrodes are shown as black areas on the electrodes. The maximum distance between the most distance and the most proximal contact is 15 mm for the electrode of type A and 7.5 mm for the electrode of type B.

Step 7:

Reduce surface distance matrix by eliminating entries where the surface distance is too high to be covered by the electrodes available (i.e. where the target region distance data indicates that the distance between the target regions is larger than for example the maximum distance between contacts of the electrode), filter out resulting pairs of target regions (if there is more than one pair check for triplet-target or quadruple-target configurations).

Step 8:

Set the initial search resolution to half the diameter of the smallest diameter available electrode type listed in the sparse surface distance matrix after step 6 (this step is executed for both computational efficiency and surgical reasons, it is almost meaningless to plan with surgically relevant differences of below 0.5 mm).

Example: 1.3 mm Diameter Defines a 0.65 mm Search Resolution

Step 9:

Determine the centre of mass (centroid) coordinates (x, y, z) of all stimulation target fields TV1, . . . , TVN.

Steps 10 to 16 correspond to determining the electric stimulation device position data.

Figure 6:
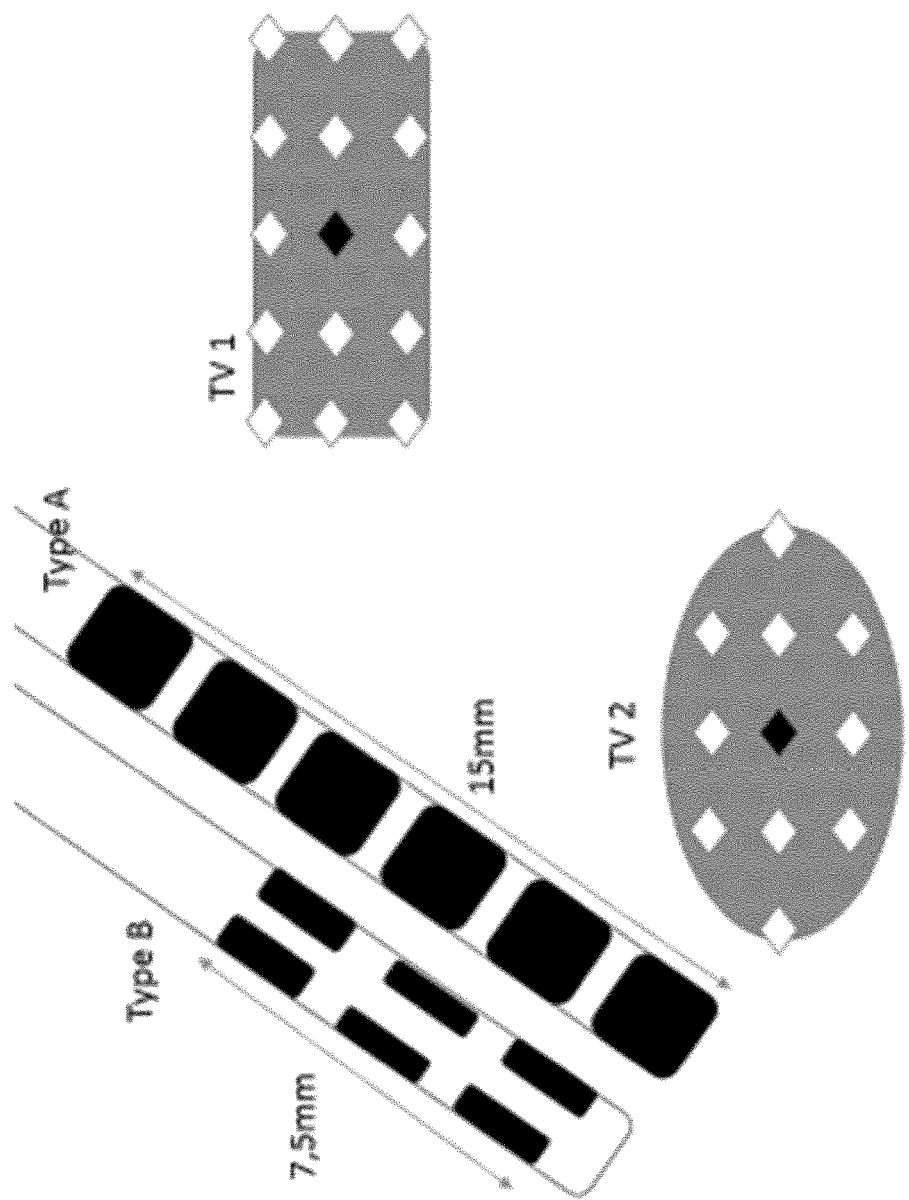

Step 10 is explained with reference to FIG. 6.

Step 10:

Determine three-dimensional search lattice by determining all points which are within the volumes TV1, . . . , N and are in x/y/z steps of the length of the search resolution distance from the centre of mass coordinates (again this assumes a penetration model where the leads are to penetrate the target volumes with at least one contact, in one alternative preferred embodiment in a touch model the target volumes can be inflated by the value of the contact diameter and run with the same calculation). This step corresponds to determining the search region data with search regions formed by lattices. A search lattice may have a basic shape of a cube and in one example is defined in rectangular coordinates, even though a definition in spherical coordinates also is conceivable.

Example

Left STN: 5 points

Right STN: 6 points

Left SN: 8 points

Right SN: 7 points

Figure 7:
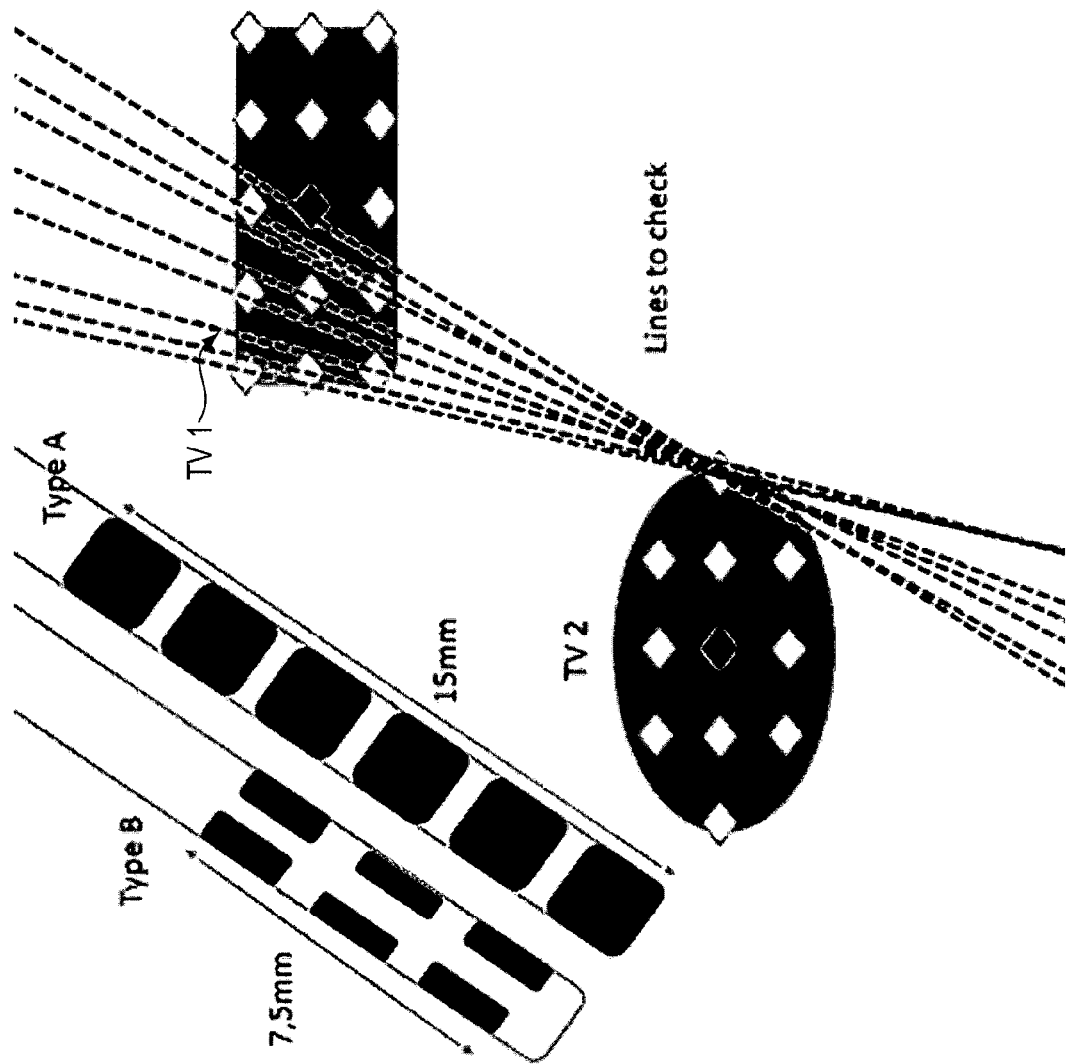

Step 11 is explained with reference to FIG. 7.

Step 11:

Determine whether there are lines (potential surgical trajectories) which connect the pairs of lattice points identified in step 6 and do not intersect with the volumes defined in avoidance field(s) AV1, . . . , AVN.

b. Example: Pairs: leftSN+leftSTN, rights+rightSTN

1. For leftSN+leftSTN there are 5*8=40 lines to check.
2. For rightSN+rightSTN there are 6*7=42 lines to check.

Figure 8:
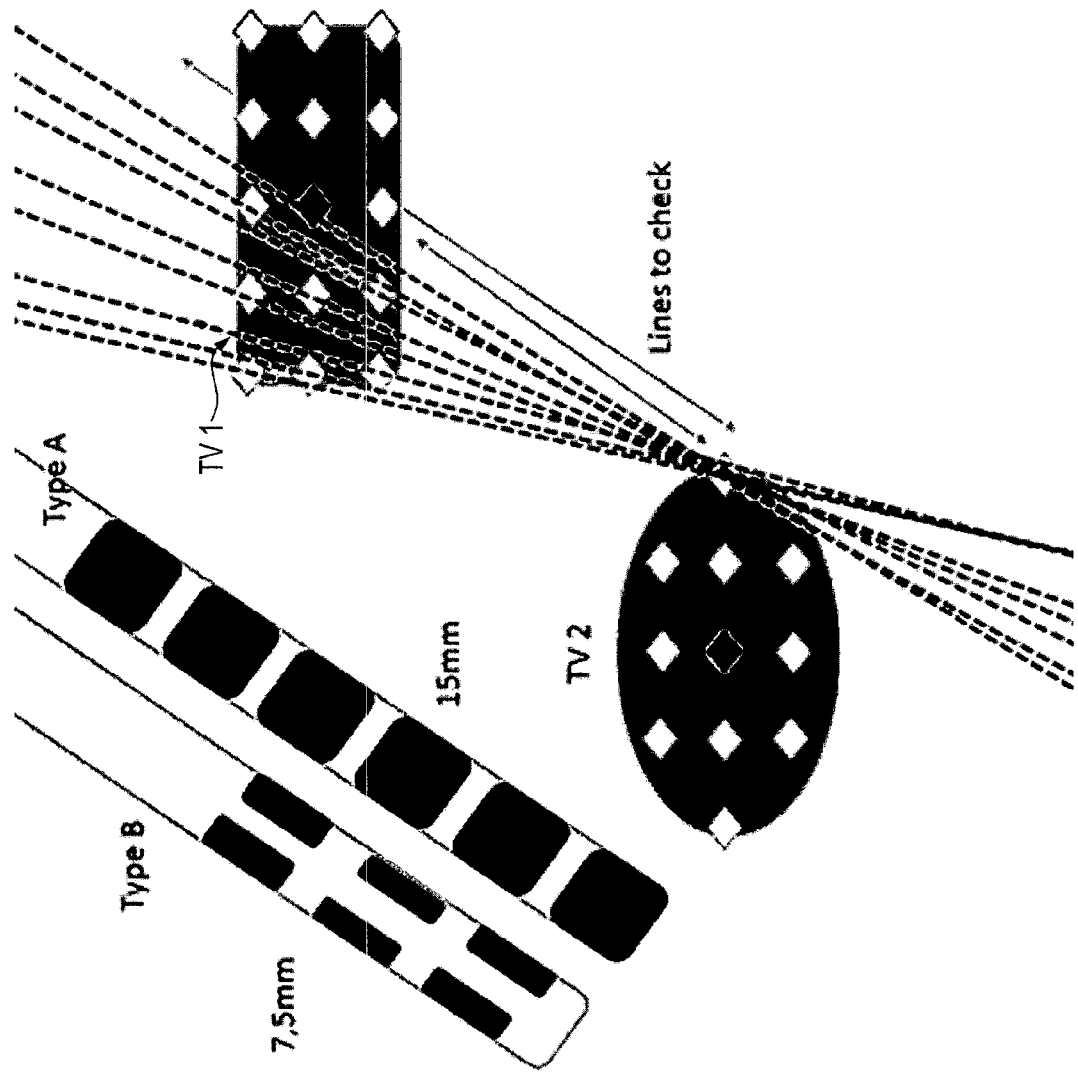

Step 12 is explained with reference to FIG. 8.

Step 12:

The remaining lines constitute viable surgical trajectories (which are defined by the electric stimulation device position data), now for each viable surgical trajectory field simulations are conducted for all available electrode types. A condition for determining that a line constitutes a viable trajectory is for example that it does not intersect an avoidance region and that it intersects at least one lattice point in each search region.

Example: Remaining 1. for leftSN+leftSTN are 3 trajectories.
2. for rightSN+rightSTN are 2 trajectories.

Step 13 is explained with reference to FIG. 9.

Step 13:

Generate virtual lead position simulations for each lead type
1. 5 lead position simulations for linear electrode (3 for leftSN+leftSTN, 2 for rightSN+rightSTN)
2. 5 lead position simulations for directional electrode (3 for leftSN+leftSTN, 2 for rightSN+rightSTN)

Figure 10:
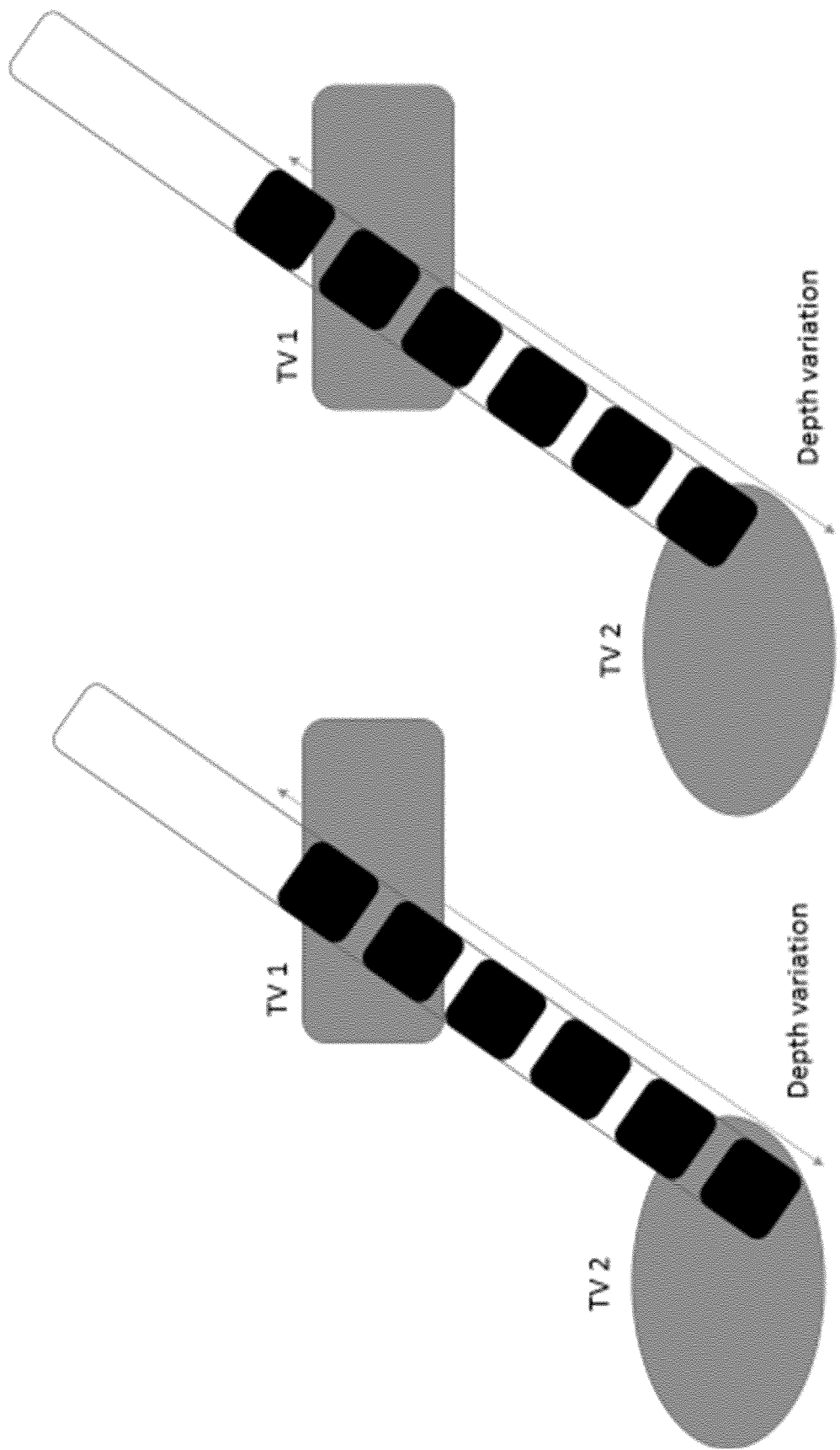

Step 14 is entirely optional and explained with reference to FIG. 10.

Step 14:

Along the viable trajectories the depth of electrode placement can be varied in a step size that is equivalent to the smallest electrode current steering increment/decrement (for sEEG electrodes contact-to-contact distance can be used) if the most distant surface points on the line intersecting with all "paired" target regions is smaller than the maximal contact distance of that electrode type:
1. For the 3 trajectories viable for leftSN+leftSTN the maximal distances on the surface are
   a. Trajectory 1: 2 mm (both linear and directional lead can be varied in depth placement and still have contacts within target volume)
   b. Trajectory 2: 3 mm (both linear and directional lead can be varied in depth placement and still have contacts within target volume)
   c. Trajectory 3: 8 mm (only linear lead can be varied in depth placement and still have contacts within target volume, directional lead has a max distance of 7.5 mm)
2. Repeat for all other pairs of target regions.

Figure 11:
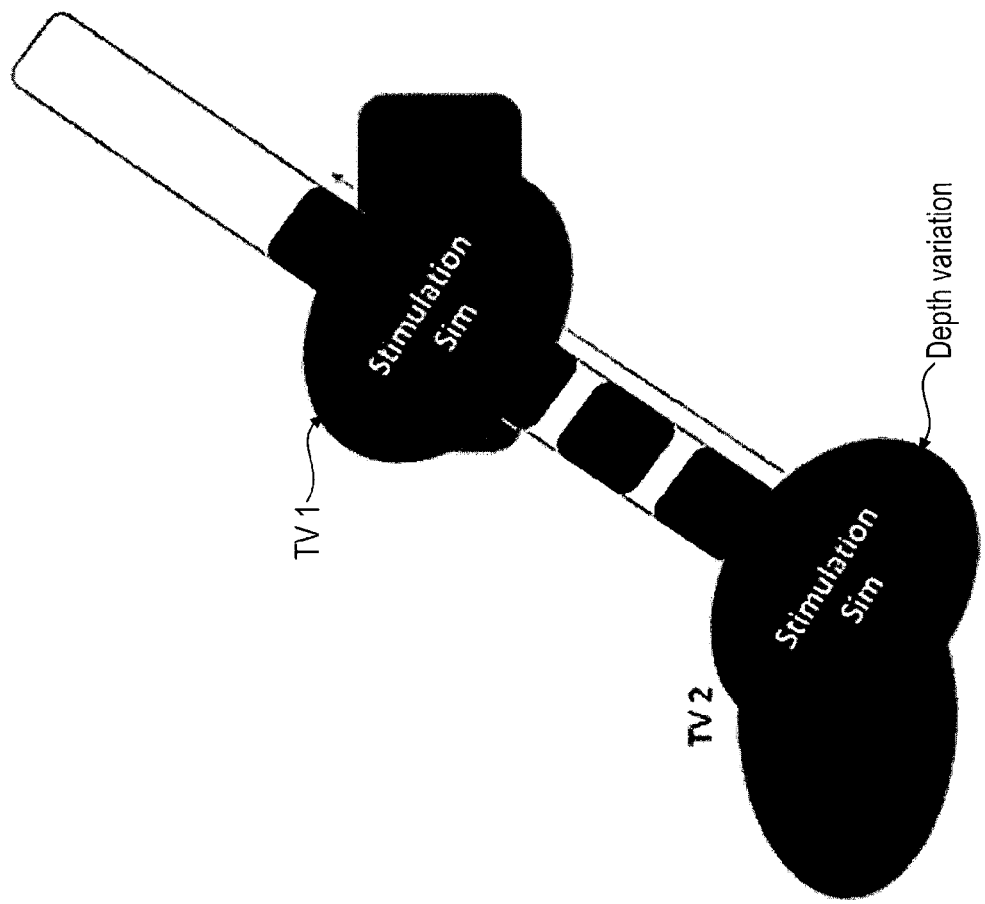

Steps 15 and 16 are explained with reference to FIG. 11.

Step 15:

The resulting list details which trajectory can be used with which type of lead for which pair of target regions.

Example

1. Trajectory 1: leftSN+leftSTN, directional and linear leads possible, both can be varied in depth
2. Trajectory 2 leftSN+leftSTN, directional and linear leads possible, both can be varied in depth
3. Trajectory 3: leftSN+leftSTN, linear lead possible, directional lead not possible, because linear lead can be varied in depth Step 16:

Now check along the length with variation of smallest increment step size (e.g. 0.5 mm) which stimulation configurations are possible for that position and display power consumption, coverage and spillage (the boundary conditions to be met by the optimization usually include maximum coverage and minimum spillage of the stimulation field). This step uses user input of boundary conditions (constraints) (e.g. all variable except stimulation pulse width which is set to 60 ms). Step 16 is entirely optional.

Example

1. Trajectory 1 can reach the targets with both direct and linear lead types and allows for depth variations, the number of depth increments is e.g. 10 for the L type and 5 for the directional type lead (because it is shorter less steps can be simulated which would still reach both targets)
2. For each of the positions (10 for a linear lead, 5 for a directional lead) possible stimulation simulations are executed (e.g. via GUIDE) and the coverage of the stimulation targets is stored (e.g. Dice coefficient of fields), this optimization problem can be solved via
   a. Brute force
   b. Region-growing approach where the contact closest to the target volume/field centroid is selected and stimulation simulations are varied from that starting point
   c. A genetic algorithm with the followings variables selected: contact (at least one of type or identity), anode, cathode configuration, current (mA), current/voltage distribution onto contacts, pulse width and frequency (user selections or fixing of a subset of these variables can constrain the search)
3. Depending on the lead type alternating or simultaneous stimulations can be simulated.

A pseudocode representation of a program for executing the brute force approach is as follows (lines starting with "%" are comments):

```
For t=1:numberofTrajectories
% number checked in Step14
% Variation=Array containing mm values that have been determined in Step 14 for
% each lead type per Trajectory.
% Calculated as Trajectory_depth_maximum (deepest from brain surface with
% contacts still in targets) minus Trajectory_depth_minimum ("highest" along with
% contacts still in targets)
RunTypes=[1 1];
%RunTypes Array is set to 1 and 1 since for both types of electrodes (directional and
%linear) positioning simulations for this trajectory are possible (Step 14 as well) and
%shall be executed.
StepSize= 0.5;
% StepSize variable set in mm, e.g. 0.5
For a=1:length (nonzero(RunTypes))
RunNumbers(a)=Variation(a)/StepSize;
end
% e.g. RunNumber(1)=2 mm / 0.5 mm;
RunNumber(1)=4;
For K=1:nonzero(RunTypes)
For times=1:RunNumbers(K)
Depth_forLeadType(K)=Trajectory_depth_maximum+((times-1)*StepSize);
% Genetic_Optimization
D=0;
%optimize and store all volume intersections at this depth for this given leadtype
Delta_Fitness=1;
While Delta_Fitness>0
```

```
D=D+1;
Position_to_be_tested= Depth_forLeadType(K);
Lead=LeadType(K);
% fitness is optimized so that Fitness is best (lowest) if PowerNeeded is minimal but
% combined target coverage in % of both targets is highest, W1 and W2 can be user
% defined weights, whether coverage of targets is more important or e.g. battery life
% Fitness=f(PowerNeeded,Combined_%_Target_Coverage,W1,W2);
[stored_configs{D}]=Genetic_Optim(Position_to_be_tested,LeadType,TargetA,Target
B,Fitness);
If D>1
Delta_Fitness=stored_configs{D}.Fitness- stored_configs{D-1}.Fitness;
end
end
%at some point all simulations are complete or there is no change in fitness, now
% take the X best fitness configurations and store them
Results=sort(stored_configs{D},Fitness);
Leadassessment{times}=Results(1:10);
% display all possible coverages and take a look which one is optimal
end
end
% system can either display Leadassessment{times} for all lead types and
% trajectories and allow user to choose the best approach or select automatically.
```

Step 17:

Finally, for each trajectory a list is made available to the user detailing the available lead types for the trajectory, as well as possible depth placement scenarios and associated power consumption, various sortings can be executed with the energy efficient and surgical safety sorting being the default (the best trajectory is the safest which touches both targets and needs the least energy to achieve optimal coverage with minimal spill)

Example

1. Trajectory 1: leftSN+left STN, directional lead, depth 0 mm above lower target boundary, coverage leftSN 85%, spill 15%, coverage left STN 90% spill 10%; configuration: C1—(IPG +), current 2 mA (60 ms pulse width, frequency 130 Hz), C3—(IPG +), current 2 mA (60 ms pulse width, frequency 130 Hz)
2. Etc. (corresponding results for other trajectories)

Figure 12:
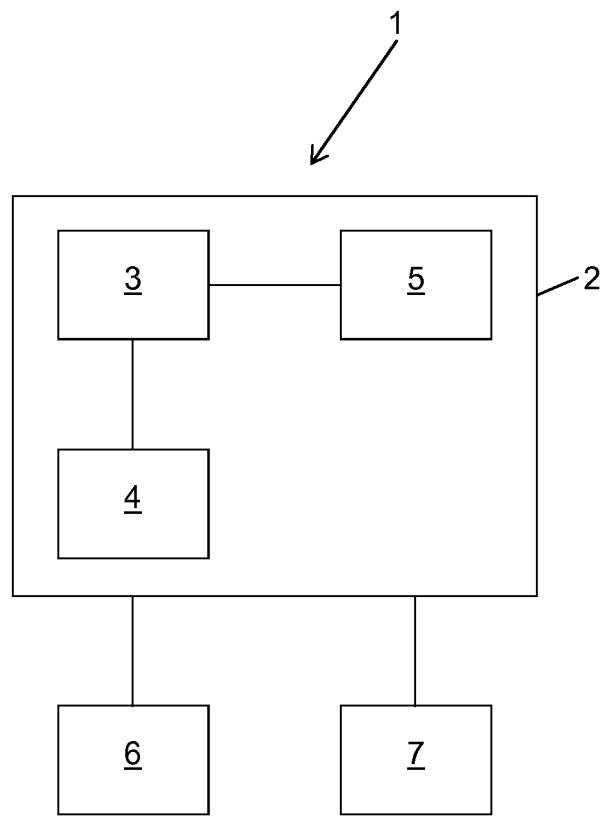
FIG. 12 illustrates the system according to the eighth aspect.

FIG. 12 shows a principle configuration of the system 1 in accordance with the eighth aspect: the system 1 comprises a computing environment 2 including at least one computer 3 having at least one digital electronic processor which is operably coupled to at least one electronic data storage device 5 and an output device 4 (e.g. a graphical output device such as a display). The electronic data storage device 5 stores at least one of the medical image data or the electric stimulation device geometry data or the atlas data. The computer 3 is configured to output, to the output device 4, electronic signals representing a graphical representation of a result of the data processing conducted by the computer 3, e.g. of the electric stimulation device position data. Furthermore, the computing environment 2 can be coupled to a measurement device 6 such as an induction coil and the electric stimulation device 7 such as an electrode.

The disclosed method and system have for example the following features:

1. Universal Atlas segmentation of patient dataset
2. Selection of target region(s)
3. Drawing target/stimulate & avoid areas or obtaining them from statistical or rule-based information sources
4. —this can be extended with known test areas/points for subsequent testing or recording points for a Micro-Electrode Recording (MER), specifically relevant for side effect regions and awake surgery
5. First selection of leads that can be used occurs, all lead types that cannot produce the desired stimulation field are discounted
6. Propose stimulation fields fitted to target and avoidance regions
7. Allow selected tolerance (field imprecision) and propose possible trajectories fitting in and reaching proposed stimulation fields sorted by chosen device
8. Rank selection on the basis of avoidance of critical structures from the Universal Atlas segmentation (ventricles, blood vessels, sulcus entry etc.) and by optimal coverage
9. Propose trajectories for validation and check In one preferred embodiment of the disclosed method, the user starts off with reviewing the area to be stimulated on radiographic imaging and paints the stimulation target zone. Now the user toggles through pre-loaded devices and can review for each device a number of possible surgical approach trajectories (which are ranked by surgical safety) and review the stimulation settings and power consumption necessary. In the next step the user selects the device (e.g. directional vs linear electrode) and reviews the now possible lead trajectories in order to select the approach.

In one preferred embodiment elastic image fusion based simulations of brain shift patterns are employed in addition to rate surgical trajectories on the basis of their robustness to occurring brain shift for the e.g. second surgical incision.

The disclosed method and system have for example the following technical effects: Trajectory planning process is massively shortened and device selection is put on a quantitative basis, rather than subjective user choice. The trade-offs device selection, optimal coverage and surgically safe trajectories are balanced by the user to reach the optimal patient outcome. For the selected electrode model and planned targets/avoidance regions resulting in a semi-automatic planning process that standardizes the trajectory selection rational with a transparent rule set. Furthermore, the disclosed method allows a user to select a suitable electrode for stimulating the target regions based on the output of the disclosed data processing, specifically based on whether a desired electrode placement can be achieved by an electrode of the type described by the electricstimulation device geometry data.

The invention claimed is:

1. A computer-implemented method for planning a position of an electric stimulation device for neurostimulation of at least two target regions disposed in an anatomical body part of a patient's body, the electric stimulation device comprising at least two electric contacts, comprising executing on at least one processor of at least one computer the steps of:
acquiring, at the at least one processor, medical image data describing a digital image of the anatomical body part, wherein the anatomical body part contains at least two target regions;
determining, by the at least one processor and based on the medical image data, target position data describing a position of each target region in the anatomical body part;
acquiring, at the at least one processor, electric stimulation device geometry data describing a distance between the at least two electric contacts of the electric stimulation device;
determining, by the at least one processor and based on the target position data, target distance data describing a distance between each pair of the at least two target regions;
determining, by the at least one processor and based on the target position data and the target distance data and the electric stimulation device geometry data, electric stimulation device position data describing a stimulation position which is a relative position between the at least two target regions and the electric stimulation device which allows for stimulation of the at least two target regions by the electric stimulation device.

2. The method according to claim 1 wherein each of the at least two target regions contains at least one nerve fibre.

3. The method according to claim 1, further comprising:
acquiring, at the at least one processor, atlas data describing an image-based model of the anatomical body part, wherein the method comprises at least one of:
i) determining, by the at least one processor and based on the atlas data and the medical image data, the target position data; or
ii) determining, by the at least one processor and based on the atlas data and the medical image data, avoidance region data describing the position of at least one avoidance region in the anatomical body part.

4. The method according to claim 3 wherein,
when the method comprises step i), the target position data is determined by applying a statistical map of potential target positions in the image-based model described by the atlas data, or by applying a segmentation of the atlas data describing a position of at least one potential target region in the image-based model, to the medical image data, and wherein,
when the method comprises step ii), the avoidance region data is determined by applying a statistical map of positions of potential avoidance regions in the image-based model described by the atlas data, or by applying a segmentation of the atlas data describing a position of at least one avoidance region in the image-based model, to the medical image data.

5. The method according to claim 3, further comprising:
determining, by the at least one processor and based on the target position data, search region data describing each one search region around the position of each one of the at least two target regions, wherein the electric stimulation device position data is determined, by the at least one processor, further based on the search region data.

6. The method according to claim 5 wherein the search regions are defined by lattices having lattice points.

7. The method according to claim 6 wherein the electric stimulation device position data is determined, by the at least one processor, by determining a plurality of trajectories which run through a lattice point of the search region associated with a first one of the at least two target regions, and run through a lattice point of the search region associated with a second other one of the at least two target regions.

8. The method according to claim 7 wherein the plurality of trajectories are straight line trajectories.

9. The method according to claim 5 wherein the stimulation position is determined by selecting, from the plurality of trajectories, one optimal trajectory which may serve as a trajectory for inserting the electric stimulation device in the anatomical body part so that coverage of the at least two target regions for stimulation by the electric stimulation device is optimal considering the distance between the at least two electric contacts.

10. The method according to claim 9 wherein the method comprises determining the avoidance region data and wherein the optimal trajectory is selected if it has a predetermined spatial relationship relative to an avoidance region in the anatomical body part.

11. The method according to claim 1 wherein the stimulation position allows for stimulation of the at least two target regions by the at least two electric contacts.

12. The method according to claim 1 wherein the target distance data is determined further based on the electric stimulation device geometry data, by considering a distance between the at least two target regions having a predetermined relationship, not larger than, the distance between the at least two electric contacts.

13. A non-transitory computer-readable program storage medium for planning a position of an electric stimulation device for neurostimulation of at least two target regions disposed in an anatomical body part of a patient's body, the electric stimulation device comprising at least two electric contacts, comprising instructions which when executed by the at least one processor causes the at least one processor to:
acquire, at the at least one processor, medical image data describing a digital image of the anatomical body part, wherein the anatomical body part contains at least two target regions;
determine, by the at least one processor and based on the medical image data, target position data describing a position of each target region in the anatomical body part;
acquire, at the at least one processor, electric stimulation device geometry data describing a distance between the at least two electric contacts of the electric stimulation device;
determine, by the at least one processor and based on the target position data, target distance data describing a distance between each pair of the at least two target regions;
determine, by the at least one processor and based on the target position data and the target distance data and the electric stimulation device geometry data, electric stimulation device position data describing a stimulation position which is a relative position between the at least two target regions and the electric stimulation device which allows for stimulation of the at least two target regions by the electric stimulation device.

14. A medical system for planning a position of an electric stimulation device for neurostimulation of at least two target regions disposed in an anatomical body part of a patient's body, the electric stimulation device comprising at least two electric contacts, the system comprising:
- at least one processor executing instructions stored on associated memory, the instructions causing the at least one processor to:
- acquire, at the at least one processor, medical image data describing a digital image of the anatomical body part, wherein the anatomical body part contains at least two target regions;
- determine, by the at least one processor and based on the medical image data, target position data describing a position of each target region in the anatomical body part;
- acquire, at the at least one processor, electric stimulation device geometry data describing a distance between the at least two electric contacts of the electric stimulation device;
- determine, by the at least one processor and based on the target position data, target distance data describing a distance between each pair of the at least two target regions;
- determine, by the at least one processor and based on the target position data and the target distance data and the electric stimulation device geometry data, electric stimulation device position data describing a stimulation position which is a relative position between the at least two target regions and the electric stimulation device which allows for stimulation of the at least two target regions by the electric stimulation device;
- at least one electronic data storage device storing at least one of the medical image data or the electric stimulation device geometry data or atlas data;
- wherein the at least one processor is operably coupled to the at least one electronic data storage device for acquiring, from the at least one electronic data storage device, at least one of the medical image data, the electric stimulation device geometry data or the atlas data.

15. The system according to the claim 14, further comprising:
- the electric stimulation device, wherein
- the electric stimulation device is operably coupled to the at least one processor for navigation of the electric stimulation device to the stimulation position.

* * * * *